(12) United States Patent
Jia et al.

(10) Patent No.: US 7,034,060 B2
(45) Date of Patent: *Apr. 25, 2006

(54) **POLYCOSANOLS FROM *ERICERUS PELA* WAX**

(75) Inventors: Qi Jia, Superior, CO (US); Ji-Fu Zhao, Littleton, CO (US)

(73) Assignee: Unigen Pharmaceuticals, Inc., Lacey, WA (US)

( * ) Notice: Subject to any disclaimer, the term of this patent is extended or adjusted under 35 U.S.C. 154(b) by 41 days.

This patent is subject to a terminal disclaimer.

(21) Appl. No.: 10/991,340

(22) Filed: Nov. 16, 2004

(65) Prior Publication Data

US 2005/0124703 A1 Jun. 9, 2005

Related U.S. Application Data

(60) Continuation-in-part of application No. 10/658,881, filed on Sep. 9, 2003, now Pat. No. 6,822,004, which is a division of application No. 10/356,676, filed on Jan. 31, 2003, now Pat. No. 6,683,116.

(51) Int. Cl.
*A01N 31/00* (2006.01)
*A61K 31/045* (2006.01)

(52) U.S. Cl. ............... 514/724; 514/164; 514/179; 514/707; 514/925; 568/840; 568/913; 568/918; 568/877; 568/923; 568/920

(58) Field of Classification Search ......... 514/724.164, 514/179, 707, 925; 568/840, 913, 918, 877, 568/923, 920
See application file for complete search history.

(56) References Cited

U.S. PATENT DOCUMENTS

| | | | |
|---|---|---|---|
| 4,714,791 A | 12/1987 | Inada et al. | |
| 5,159,124 A | 10/1992 | Bertholet | |
| 5,856,316 A | 1/1999 | Laguna Granja et al. | |
| 6,225,354 B1 | 5/2001 | Perez | |
| 6,235,795 B1 | 5/2001 | Hernandez et al. | |
| 6,465,526 B1 | 10/2002 | Hernandez et al. | |

FOREIGN PATENT DOCUMENTS

WO WO 99/48853 9/1999

OTHER PUBLICATIONS

Agarwal and Baslas (Sep.-Oct. 1981) Indian J. Pharma. Sci. 43:182-183.
Ali et al. (1979) Egypt J. Pharm. Sci. 18:93-99.
Arai et al., (1982) J. Pharm. Soc. Jp. 102:1089-1091.
Awad et al. (1993) Fitoterapia 64:553.
Baherji and Nigam (Oct. 1980) J. Indian Chem. Soc. 57:1043-1044.
Banerji and Nigam (1981) Fitoterapia 52:3-4.
Baslas and Agarwal (Mar.-Apr. 1980) Indian J. Pharm. Sci. 42:66-67.
Behari and Gupta (1980) Acta Ciencia Indica 6:226-228.
Brondze et al. (Nov.-Dec. 1983) J. Nat. Prod. 46:940-941.
Dobhal et al. (1988) Fitoterapia 59:155.
Hashimoto and Kitaoka (1983) Appl. Ent. Zool. 17:453-459.
Ismail et al. (1984) Fitoterapia 55:110-112.
Joshi et al. (1987) Herba Pol. 33:71-74.
Kang and Kim (1987) Arch Pharm. Res. 10:67-68.
Komatsu et al. (1982) Yakugaku Zasshi 102:499-502.
Krzaczek et al. (1988) Acta Soc. Bot. Pol. 57:85-92.
Kumar and Srimannarayana (Sep.-Oct. 1981) J. Nat. Prod. 44:625-628.
Makhsudova (Mar.-Apr. 1979) Chem. Nat. Compd. 15:186.
Nazir et al. (1993) Xeischrift fur Naturforschung. Section C Biosciences 48:5-9.
Nagata et al. (1994) Breeding Sci. 44:427-429.
Olaniyi et al. (1975) Planta Medica 28:186-189.
Oskay and Yesilada (1984) J. Nat. Prod. 47:742.
Pinto and Bento (Oct.-Dec. 1986) Rev Soc Bras Med Trop 19:243-5.
Prakash and Banerji (1979) Fitoterapia 50:265-266.
Rizk et al. (1980) Fitoterapia 51:223-228.
Solberg (1976) Acta Chem. Scand. B. 30:786-787.
Srinivasan and Subramanian (1980) Fitoterapia (1980) 51:241-244.
Takahashi and Nomura (1982) Entomol. Gen. 7:313-316.
Tulloch et al. (1980) Can. J. Bot. 58:2602-2615.
Tulloch (1981) Can. J. Bot. 59:1213-1221
Chenkang (Jul.-Sep. 1985) World Animal Review 55:26-33.

*Primary Examiner*—Elvis O. Price
(74) *Attorney, Agent, or Firm*—Swanson & Bratschun, L.L.C.

(57) ABSTRACT

The present invention provides a novel method for the preparation of a unique profile of primary aliphatic alcohols, having 24 to 30 carbon atoms, from the wax secreted by the insect *Ericerus pela*. Included in the present invention is the composition of matter, referred to herein as "polycosanol" produced by the method of this invention. The polycosanol composition is comprised primarily of the four primary aliphatic alcohols, tetracosanol, hexacosanol, octacosanol and triacontanol. Further included in this invention is the use of said composition of matter for the prevention and treatment of obesity, syndrome X, diabetes, hypercholesterolemia, atherosclerotic complications, ischemia and thrombosis.

5 Claims, 8 Drawing Sheets

Long Chain aliphatic alcohol

Ester of Long Chain aliphatic alcohol and Fatty acid

POLYCOSANOLS FROM *ERICERUS PELA* WAX

RELATED APPLICATIONS

This application is a continuation in part of U.S. application Ser. No. 10/658,881, filed Sep. 9, 2003, now U.S. Pat. No. 6,822,004, which is a divisional of U.S. application Ser. No. 10/356,676, filed Jan. 31, 2003, now U.S. Pat. No. 6,683,116 each of which is entitled "Polycosanols from *Ericertis Pela* Wax," and each of which is incorporated herein by reference in its entirety.

FIELD OF THE INVENTION

The present invention relates generally to a method for the generation of a composition of matter comprised of a unique profile of primary aliphatic alcohols, having 24 to 30 carbon atoms, from a novel natural source—a wax secreted by the Chinese wax soft scale insect, *Ericerus pela*, which belongs to the family Coccidae. The present invention includes the composition of matter, referred to herein as "polycosanol(s)" produced by the method of the invention. The polycosanol composition produced according to the method of this invention is comprised of primarily four primary aliphatic alcohols, tetracosanol, hexacosanol, octacosanol and triacontanol. The invention also includes the use of this composition of matter for the prevention and treatment of obesity, syndrome X, diabetes, hypercholesterolemia, atherosclerotic complications, ischemia and thrombosis.

BACKGROUND OF THE INVENTION

Polycosanols are a class of primary aliphatic alcohols having 20 to 40 (C20–C40) carbon atoms. They are widely distributed in germs, kernels and other components of nuts, seeds, fruits and cereals (Kawanishi et al. (1991) J. Amer. Oil Chemist Soc. 68:869–872), in Greek olive oils (Dimitrios et al. (1983) Grasas Aceites 34:402–404) and in apple wax (Belding et al. (1993) Hertscience 28:90). Polycosanols are also present, in very small amounts (less than 0.1%), in wheat grain, in the form of the long chain alkyl esters of fatty acids. The major compounds present in wheat grain include, palmitoyl hexacosanol and arachidoyl, palmitoyl and behenoyl tetracosanol (Ohnishi et al. (1986) Cereal Chem 63:193–196).

Polycosanols, both as the free alcohols and the esters of fatty acids, have been isolated from many different genera and species of plants, including from the species *Achillea biebersteinii* (Oskay and Yeslada (1984) J. Nat. Prod. 47:742), *Calamagrostis arundinacea* (Solberg (1976) Acta Chem. Scand Ser. B. Org. Chem. Bioche. 30:786-787), *Emilia sonchifolia* (Srinivasan and Subramanian, (1980) Fitoterapia 51:241–244), *Heliotropium digynum* (Ismail et al. (1984) Fitoterapia 55:110–112), *Hypericum perforatum* (Brondze (1983) J. Nat. Prod. 46:940–941), *Tragopogon orientalis* (Krzaczek et al. (1988) Acta Soc. Bot. Pol. 57:85–92), and from the genera of Triceae (Tulloch (1981) Can. J. Bot. 58:2602–2615). Polycosanols have also been isolated from various parts of many different genera and species of plants, including from the bark of various Acacia species (Banerji and Nigram (1980) J. Indian Chem. Soc. 57:1043–1044); from the stem of *Anisomeles indica* (Dobhal et al. (1988) Fitoterapia 59:155); from the leaves of *Cordia rothii* (Behari et al. (1980) Acta Cienc. Indica Chem. 6:226–228), *Hibiscus cannabinus* (Makhsudova (1979) Chem. Nat. Compd. 15:186) and *Holigarna arnottiana* (Prakash and Banerji (1979) Fitoterapia 50:265–266); from the roots of *Talinum paniculatum* (Komatsu et al. (1982) Yakugaku Zasshi 102:499–502); from the leaves and roots of *Gymnosporia Montana* (Kumar and Srimannarayana (1981) J. Nat. Prod. 44:625–628); from the aerial parts of *Cymbopogon citrates* (Olaniyi et al. (1975) Planta Medica 28:186–189), *E. merifolia* (Baslas and Agarwal (1980) Indian J. Pharm. Sci. 42:66–67) and *E. Peplus* (Rizk et al. (1980) Fitoterapia 51:223–228), *Portulaca suffruticosa* L. (Joshi et al. (1987) Herba Pol. 33:71–74) and *Youngia denticulate* (Arai et al. (1982) J. Pharm. Soc. Jp. 102: 1089–1091); and from the heartwood of *Melia birmanica* (Banerji and Nigam, (1981) Fitoterapia 52:3–4). Polycosanols have also been isolated from carnauba wax from exudates of the leaves of the palm tree *Copernicia cerifera* (Pinto and Bento (1986) Rev Soc Bras Med Trop 19:243–5), from the leaf wax of *Euphorbia helioscopia* (Nazir et al. (1993) Xeischrift fur Naturforschung. Section C Biosciences 48:5–9), from epicuticular waxes of genera of Gramineae (Tulloch (1981) Can. J. Bot. 59:1213–1221), and from and the latex of *Euphorbia pseusocactus* (Awad et al. (1993) Fitoterapia 64:553) and *Euphorbia thymifolia* (Agarwal and Maslas (1981) Indian J. Pharma. Sci. 43:182–183). Finally, polycosanols have been isolated from the Korean indigenous plant *Echinosophora koreensis* (Kang and Kim (1987) Arch Pharmacal Res. 10:67–68).

Bertholet has described a method for preparing polycosanol compositions by means of the saponification of plant wax from rice bran wax, carnauba wax and jojoba oil. (Bertholet, U.S. Pat. No. 5,159,124 (1991)). In the method described by Bertholet, the plant wax was first dissolved in an organic water immiscible solvent, such as butanol or pentanol, and then hydrolyzed using an aqueous solution of an alkaline earth metal hydroxide. The fatty acid by products of the saponification reaction are soluble in the alkaline aqueous layer and the polycosanol alcohol product remains in the organic layer, which contains <10% fatty acids and >90% alcohols. The overall yield of the reaction was approximately 50%. The composition of the polycosanol product is dependent on the origin of the plant wax.

N-hexacosanol has been isolated from wool wax hydrosylate mixtures using gel permeation chromatography (Steel et al. (1999) International Publication No. WO 99/48853).

Polycosanol compositions isolated from rice bran wax have been formulated with phytosterol from vegetable oil and used for reducing cholesterol levels. The aliphatic alcohol profile of this material is approximately 23–33% total polycosanol. Triacontanol is the major compound (8–9%), followed by octacosanol (5–6%) and tetracontanol, hexacosanol, dotriacontanol and tetratriacosanol (2–5% each). (Sorkin Jr. (1999) U.S. Pat. No. 6,197,832, and Sorkin Jr. (1998) U.S. Pat. No. 5,952,393). Octacosanol isolated from Sinach has been formulated with other ingredients as a nutritional powder for boosting energy. (Gaynor U.S. Pat. No. 5,744,187 (1996)).

Sugar cane provides a major natural source of commercial polycosanol products (Ali et al. (1979) Egypt J. Pharm. Sci. 18:93–99). The long chain aliphatic alcohols are located primarily in the wax layer of sugar cane, with octacosanol being the predominant compound (Nagata et al. (1994) Breeding Sci. 44:427–429) (See Table 1, below). Aliphatic alcohols from sugar cane wax can be extracted directly with a supercritical fluid, an organic solvent or an alcohol to obtain a mixture with octacosanol (7–10%) and triacontanol (0.4–1%) as the major components (Inada et al. (1986) U.S. Pat. No. 4,714,791). A mixture of higher primary aliphatic alcohols, having from 24 to 34 carbon atoms has been obtained by saponification of sugar cane wax. (Laguna et al. (1996) U.S. Pat. No. 5,856,316). The saponification reaction described included melting the sugar cane wax, forming a homogeneous phase with an alkaline earth hydroxide (5–30%), extracting with an organic solvent and recrystallizing from an organic solvent. The profile of the material included octacosanol as the major component (60–70% content), followed by triacontanol (10–15%), hexacosanol (5.5–8.5%), dotriacontanol (4–6%), heptacosanol (2–3.5%), tetratriacontanol (0.4–2.0%), nonacontanol (0.4–1.2%) and tetracosanol (0.5–1.0%). This material has been formulated with acetylsalicylic acid and used for the treatment of hypercholesterolemia, atherosclerotic complications, gastric ulcers and to improve male sexual activity. (Laguna et al. (1996) U.S. Pat. No. 5,856,316).

*Ericerus pela*, which belongs to the family Coccidae (Ben-Dov and Hodgson, (1997) Soft scale insects; their biology, natural enemies and control. Vol. 7A. Elsevier Science Publishers, Amsterdam), is an insect indigenous to southern China, having the common name white wax scale. (Zhang (1987) Scientia Silvae Sinica 23:383–385, Cen and Ji (1988) Insect Knowledge 25:230–232). This insect has a high economic value in China (Chen (1999) World Forest Res. 12:46–52), due to its ability to produce wax and its high nutritional value (Zhao et al. (2001) Entomological Knowledge 38:216–218). The female lays over 7000 eggs on average (Park et al. (1998) Korea J. Applied Entomology 37:137–142) and egg hatching is directly related to wax production (Chen et al. (1997) Forest Res. 10:149–153). The reproductive capability of *Ericerus pela* can be impacted by sex ratio, lifespan, habitat and other ecological conditions. (Zhang et al. (1993) Entomological Knowledge 30:297–299). The eggs from this insect contain a high percentage of proteins (40–55%) and amino acids (30–50%) and are nutritious and safe for human consumption. (Ye et al. (2001) Forest Res. 14:322–327). The insect can be raised on 200 different species of host plants belonging to 98 genera and 36 families. (Chen and Li (2001) Forest Res. Beijing 14:100–105). The host plants provide not only their habitat and reproductive sites, but also serve as their food source. (Chen et al. (1997) Forest Res. 10:415–419). The average amount of wax production is affected by the host plant species (Chen et al. Forest Res. 11:285–288), geographic varieties of the insect (Chen et al. (1998) Forest Res. 11:34–38) and climate conditions, particularly temperature, dryness and intense sunshine. (Liu et al. (1998) Forest Res. 11:508–512). *Ericerus pela* has been produced in commercial forest plantations and the conditions and value of crop production have been reported. (Liu et al. (1996) Forest Res. 9:296–299).

The wax from *Ericerus pela* is secreted from the wax gland of both male and female insects. (Tan and Zhong (1992) Zoological Res. 13:217–222). The composition of the insect wax has been analyzed by GC/MS and determined to be hexacosyl hexacosanoate (55.16%), hexacosyl tetracosanoate (22.36%) and hexacosyl octacosanol (16.65%). (Takahashi and Nomura (1982) Entomol. Gen. 7:313–316). The wax has traditionally been used for bleeding, pain relief, wound healing, coughing and diarrhea. (Li (1985) World Animal Review 55:26–33). Saturated long chain fatty alcohols have also been found in other insects, including *Drosicha corpulenta* (Hashimoto and Kitaoka (1983) Appl. Entomol Zool. 17:453–459).

Bee wax also contains a significant quantity of long chain primary alcohols in both the free and esterified forms. Polycosanol compositions isolated from bee wax contain 24 to 34 carbon atoms (C24–C34) comprised of tetracosanol (9–15%), hexacosanol (12–18%), octacosanol (13–20%), triacontanol (20–30%) and dotriacontanol (13–21%). (Hernandez et al., U.S. Pat. No. 6,235,795 (1994)). Bee wax, formulated with olive oil, β-sitosterol and an extract from *Coptis chinensis*, has been used for the treatment of diaper rash (Niazi, U.S. Pat. No. 6,419,963 (2001)) and as a pharmaceutical and cosmetic carrier (Xu, U.S. Pat. No. 5,817,322 (1996)). Polycosanols isolated from bee wax also show anti-ulcer and anti-inflammatory activity. (Mas (2001) Drugs of the Future, 26:731–744; Carbajal et al. (1996) J. Pharmacy and Pharmacol. 48:858–860; Hernandez et al., U.S. Pat. No. 6,235,795 (1994)).

Polycosanol compositions isolated from bee wax upon saponification contain primarily octacosanol (13.0–20.0%), triacontanol (20–30%), dotriacontanol (13–21%), hexacosanol (12–18%), tetracosanol (9–15%) and tetratriacontanol (1.5–3.5%). (Hernandez et al., U.S. Pat. No. 6,465,526 (2000)). In the method reported by Hernandez et al., the saponification reaction was performed in the homogeneous phase using a 4–7:1 wax:base ratio. After hydrolysis, the polycosanols were extracted with organic solvents to produce a product that contained 80–98% total polycosanols in a yield of approximately 30% from bee wax. (Hernandez et al., (1994) U.S. Pat. No. 6,235,795). As noted above, this material showed both anti-ulcer and anti-inflammatory activity. Polycosanol compositions obtained from the saponification of bee wax have also been formulated with acetyl salicylic acid for use in the treatment of hypercholesterolemia, atherosclerotic complications, gastric ulcers and to improve male sexual activity (Granja et al., U.S. Pat. No. 5,663,156 (1994)).

The polycosanols in bee wax have also been extracted directly with organic solvent without saponification. (Perez, U.S. Pat. No. 6,225,354 (1999)). This material contained octacosanol (30–60%), triacosanol (16–26%), dotriacontanol (13–22%) and hexacosanol (7–12%) as the major components and has been shown to be effective in the treatment and prevention of hypercholesterolemia related diseases. (Perez, U.S. Pat. No. 6,225,354 (1999)).

Polycosanol compositions isolated from sugar cane have been shown to lower cholesterol levels in both animal and human models. (Menedez et al. (2000) Br. J. Clin. Pharmacol. 50:255–262; Arruzazabala et al. Braz. J. Med. Biol. Res. 33:835–840; Crespo et al. (1999) Int. J. Clin. Pharmacol. 19:117–127; Gouni-Berthold and Berthold (2002) Am. Heart J. 143:356–365; Alcocer et al. (1999) Int. J. Tissue React 21:85–92). Modulation of 3-hydroxy-3-methylglutaryl-Coenzyme A (HMG-CoA) reductase was observed in a celline model, but not in a pure enzyme inhibition assay. (Menendez et al. (2001) Arch. Med. Res. 32:8–12). Instead of inhibiting of 3-hydroxy-3-methylglutaryl-Coenzyme A (HMG-CoA) reductase, as most cholesterol lowering drugs, polycosanol may have different mechanism of action, such as the down regulation of HMG-CoA reductase production in gene expression and/or at the proteomic level. (McCarty (2002) Med. Hypotheses 59:268).

Older patients with hypertension and Type II hypercholesterolemia, treated with polycosanol compositions isolated from sugar cane at a dosage of 20 mg/day for twelve months, showed significantly decreased TC, LDL, LDL/HDL and TC/HDL levels, and increases HDL levels. (Castano et al. (2002) Drug R D. 3:159–172; Castano et al. (2001) Int. J. Clin. Pharmacol. 21:43–57). Even at a dosage of 5–10 mg, polycosanol compositions isolated from sugar cane showed a significant benefit in hypercholesterolemia postmenopausal women (Mirkin et al. (2001) Int. J. Clin. Pharmacol. 21:31–41; Castano et al. (2000) Gynecol. Endocrinol.

14:187–195) and in high coronary risk older patients (Castano et al. (2001) J. Geontol A Biol. Sci. Med. Sci. 56:M186–192; Castano et al. (1999) Int. J. Clin. Pharmacol. 19:105–116). In summary, it has been proposed that polycosanol compositions isolated from sugar cane could potentially provide a new treatment for cardiovascular disease with equal or better clinical output than simvastatin, pravastatin, lovastatin, probucol and acipimox. (Janikula (2002) Altern. Med. Rev. 7:203–217).

Polycosanol compositions have also been shown to exhibit anti-thrombic effects (Carbajal et al. (1998) Pharmacol. Res. 38:89–91), with significant inhibition of platelet aggregation (Arruzazabala et al. (1993) Thromb Res. 69:321). Additionally, unlike aspirin polycosanol did not affect the platelet anti-aggregating enzyme PGI2, but rather inhibited platelet aggregating enzyme thromboxane B2 (TXB2). (Carbajal et al. (1998) Prostaglangins Leukot. Essent Fatty Acids 58:61–64). This makes a combination therapy of polycosanol with aspirin an attractive option. (Arruzazabala et al. (1997) Pharmacol. Res. 36293–297). For other reports on the anti-thrombic effects of polycosanol compositions see Arruzazabala et al. (2002) Clin. Exp. Pharmacol. 29:891–7; Janikula (2002) Alternative Medicine Review 7:203–217; and Stusser et al. (1998) Int J Clin Pharmacol Ther 36(9):469–73). For reports on other cardiovascular benefits of polycosanol compositions see Noa et al. (1997) J. Pharm. Pharmacol. 49:999–1002; Noa et al. (2001) Pharmacolo. Res. 43:31–37; Molina et al. Braz. J. Med. Biol. Res. 32:1269–1276; Janikula (2002) Alternative Medicine Review 7:203–217; and Menendez et al. (2002) Can J Physiol Pharmacol. 80:13–21.

Polycosanol(s) and polycosanolic acids have also been reported to be effective as nutritional and therapeutic preparations for the prevention and treatment of aging and related conditions, such as, atherosclerosis, hypertension, diabetes, tumors, obesity, overweight, hypertriglyceridemia, hypercholesterolemia, as well as other conditions. (Pistolesi, WO 02/052955 (2001)). There are a numerous other reported uses of individual polycosanols and mixtures thereof in the literature. This provides a significant incentive to develop new sources containing novel polycosanol compositions of matter, which would be expected to have different pharmacological effects and strengths. The multitude of uses for the individual alcohols and mixtures thereof, also provides a significant incentive to develop improved methods for isolating these compounds.

Polycosanol has been determined to be safe at a dosage of up to 500 mg/kg/day, which is 1500 times greater than the standard human dosage of 20 mg/day. Rats treated with a dosage of 500 mg/kg/day for 12 to 24 months exhibited no signs of toxicity or carcinogenesis resulting from treatment with polycosanols. (Aleman et al. (1995) Food Chem. Toxicol. 33:573–578). Dogs given 180 mg/kg/day for one year showed no side effects resulting from the composition (Mesa et al. (1994) Toxicol. Lett. 73:81–90) and monkeys given 25 mg/kg/day for 54 months showed no signs of adverse effects (Rodrigurz et al. (1994) Food Che. Toxicol. 32:565–575). In reproductive and fertility studies, polycosanol compositions exhibited no adverse effects on fertility, reproduction and development in rats fed up to 500 mg/kg/day for two weeks before mating, throughout pregnancy, and 21 days into lactation, and in male rats given 500 mg/kg/day for 60 days prior mating (Rodriguez and Garcia (1998) Teratog. Carcinog. Mutagen. 18:1–7). Rabbits treated with a dosage of 1000 mg/kg/day during pregnancy showed no evidence of teratogenic and embryonic toxicity. The tissue distribution of polycosanol in animal models has been reported by Kabir and Kimura. ((1995) Ann. Nutr. Metab. 39:279–284 and (1993) 37:33–38). Polycosanol has been shown to be stable in 10 mg tablets for up to nine months (Cabrera et al. (2002) Boll. Chim. Farm. 141:223–229) with no interaction with excipients (Cabrera et al. (2002) Boll. Chim. Farm. 141: 138–142).

Cholestin™, a dietary supplement from Pharmanex, contains octacosanol isolated from the wax of honey bees. This product has been shown to promote healthy cholesterol levels by inhibiting the production of cholesterol in the liver. LesstanoL™ brand from Garuda International, Inc. contains natural octacosanol (95%) isolated from sugar cane or vegetable waxes. TwinLab Octacosanol Plus is derived from spinach, a superior and all natural source of octacosanol. Octacosanol in Nature's Way's products is a naturally occurring substance found in sugar cane, wheat germ oil, spinach, and other natural sources. Octacosanol from Viable Herbal Solutions is the active ingredient in wheat germ oil and is used to increase endurance, stamina and vigor. Applicant is not aware of any reports regarding the production polycosanol compositions from *Ericerus pela* wax.

Sierra et al. has developed a gas chromatographic (GC) method for determining the fatty alcohol content of film-coated tablets. (Sierra et al. (2002) J. AOAC Int. 85:563–566). 1-Octacosanol in rat plasma has been quantified after solid phase extraction and derivatization using a capillary GC method developed by Marrero and Gonzalez ((2001) J. Chromatogr. B Biomed. Sci. Appl. 762:43–49). The polycosanols were derivatized with N-methyl-N-trimethylsilyltrifluoroacetamide. The general physical characteristics of sugar cane polycosanols have been reported by Uribarri et al. ((2002) Drug Dev. Ind. Pharm. 28:89–93).

It is an objective of this invention to provide a mixture of higher primary aliphatic alcohols, referred to herein as "polycosanol(s)" having a unique chemical composition profile.

It is another objective of this invention to provide an improved method for obtaining a highly pure mixture of higher primary aliphatic alcohols.

SUMMARY OF THE INVENTION

The present invention includes a novel method for the preparation of a unique profile of primary aliphatic alcohols, having 24 to 30 carbon atoms, from the wax secreted by the insect *Ericerus pela*. Included in the present invention is the composition of matter, referred to herein as "polycosanol" produced by the method of this invention. The polycosanol composition produced by the method of this invention is comprised primarily of two major components, the primary aliphatic alcohols, hexacosanol and octacosanol, with two minor components, the primary aliphatic alcohols, tetracosanol and triacontanol. Further included in this invention is the use of said composition of matter for the prevention and treatment of obesity, syndrome X, diabetes, hypercholesterolemia, atherosclerotic complications, ischemia and thrombosis.

The method of the present invention is comprised of the steps of (a) hydrolyzing the melted wax obtained from the insect with a base; (b) neutralizing the basic hydrosylate obtained from step (a) to yield a lower purity composition of matter comprised of polycosanols; and (c) optionally extracting the hydrosylate without neutralization with an organic solvent to obtain a higher purity polycosanol composition. In another embodiment of the instant invention, the method further comprises the step of (d) purifying the hydrolyzed product obtained in step (c) by recrystallization.

The method of this invention can be extended to the isolation and purification of polycosanol compositions from any source of wax, in particular from any source of insect wax.

The present invention includes the novel mixtures of primary long chain aliphatic alcohols (referred to herein as "polycosanol") prepared and isolated by the methods of this invention. The long chain aliphatic alcohol portions of the polycosanol compositions prepared and isolated by the methods of this invention comprise 1-hexacosanol (20%–50%), 1-octacosanol (15%–45%), 1-triacontanol (2%–10%) and 1-tetracosanol (approximately 1%–9%). The total amount of long chain aliphatic alcohols in these compositions can be anywhere in the range of 35% to 100%, depending on the level of purification of the crude extract obtained from step (b) of the described method. In one embodiment, the composition of matter is isolated following hydrolysis of the wax and neutralization with no further purification. This composition is comprised of approximately 35–55% of the long chain primary aliphatic alcohols of interest. The major components of this composition are: 1-hexacosanol (~20–30%) and 1-octacosanol (~15–25%) and the minor components are: 1-triacontanol (~2–4%) and 1-tetracosanol (~1–3%). In another embodiment, the composition of matter is isolated following hydrolysis of the wax and further purification via extraction of the polycosanols under basic conditions with an organic solvent. In this embodiment the composition of matter is comprised of approximately 75–100% of the long chain primary aliphatic alcohols. The major components of this composition are 1-hexacosanol (~30–50%), 1-octacosanol (~25–45%), 1-triacontanol (~4–10%) and 1-tetracosanol (~3–9%). In another embodiment, the composition can be even further purified by recrystallization. As noted above, the alcoholic mixtures obtained from Ericerus pela wax in accordance with the present invention can be distinguished from all other currently known sources of polycosanols. Table 1, below highlights the differences between the compositions isolated from sugar cane and bee wax, which are currently the major commercially available sources of polycosanols, with the composition isolated according to the method of this invention.

The present invention also includes the use of the polycosanol compositions isolated by the method of this invention for the prevention and treatment of obesity, syndrome X, diabetes, hypercholesterolemia, atherosclerotic complications, ischemia and thrombosis. These novel compositions are expected to have different pharmacological effects and strengths. The compositions can be formulated in a pharmaceutical composition, foodstuff or dietary supplement and administered to humans and other animals.

The present invention provides not only a novel source of polycosanols and the resulting novel compositions of matter, but also provides an improved method for extracting these compounds from a wax. Preferred levels of certain operational parameters in the extraction and purification process have been discovered which lead to further enhancement of the purity level of the isolated alcohols and enhancement of the percent recovery of the alcohols from Ericerus pela wax. These operational parameters include optimized solvent volume and quantity of basic solution in the hydrolysis process; and extraction of the basic powder of crude polycosanol with lower polarity organic solvents than those used in current methods, which is critical to obtaining higher quality insect polycosanol.

It is to be understood that both the foregoing general description and the following detailed description are exemplary and explanatory only and are not restrictive of the invention as claimed.

DETAILED DESCRIPTION OF THE INVENTION

Figure 1:
FIG. 1 depicts the chemical structure of a representative long chain (C22) aliphatic alcohol and a representative structure of an esterified fatty acid.
Figure 1:
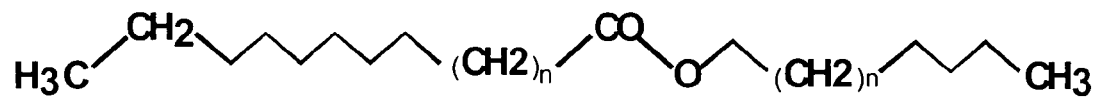
Figure 2:
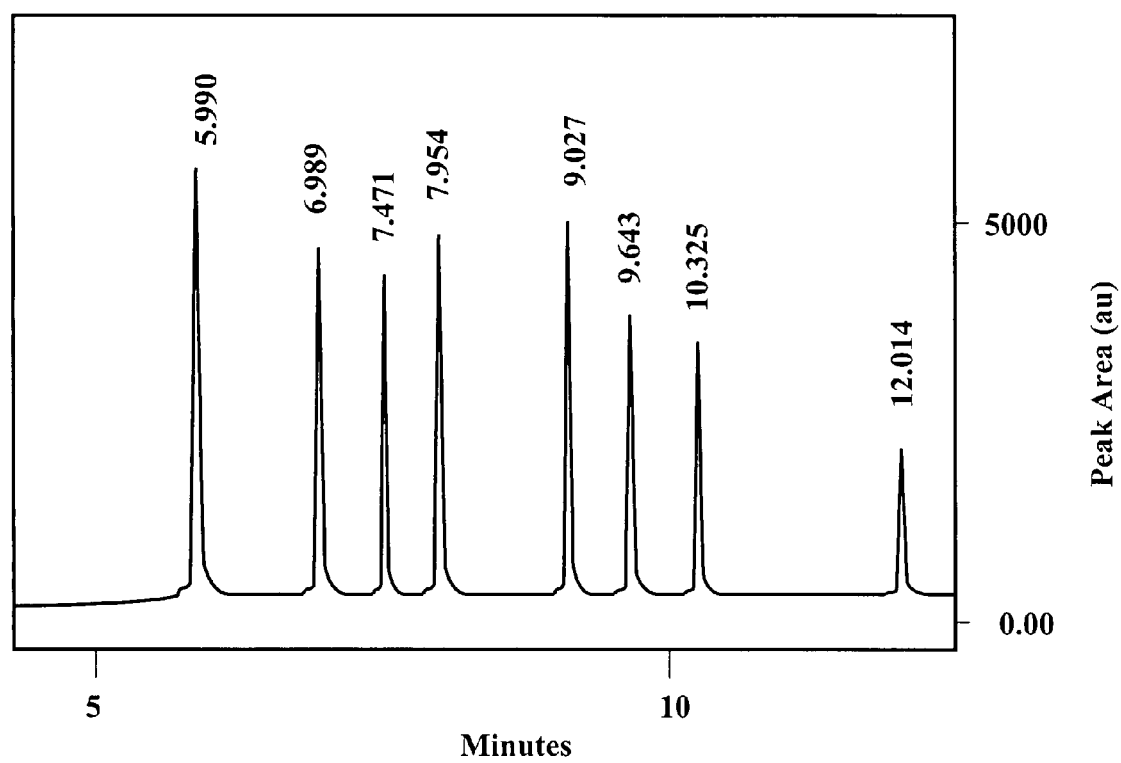
FIG. 2 illustrates the gas chromatographic (GC) profile of eight polycosanol standards.
Figure 3:
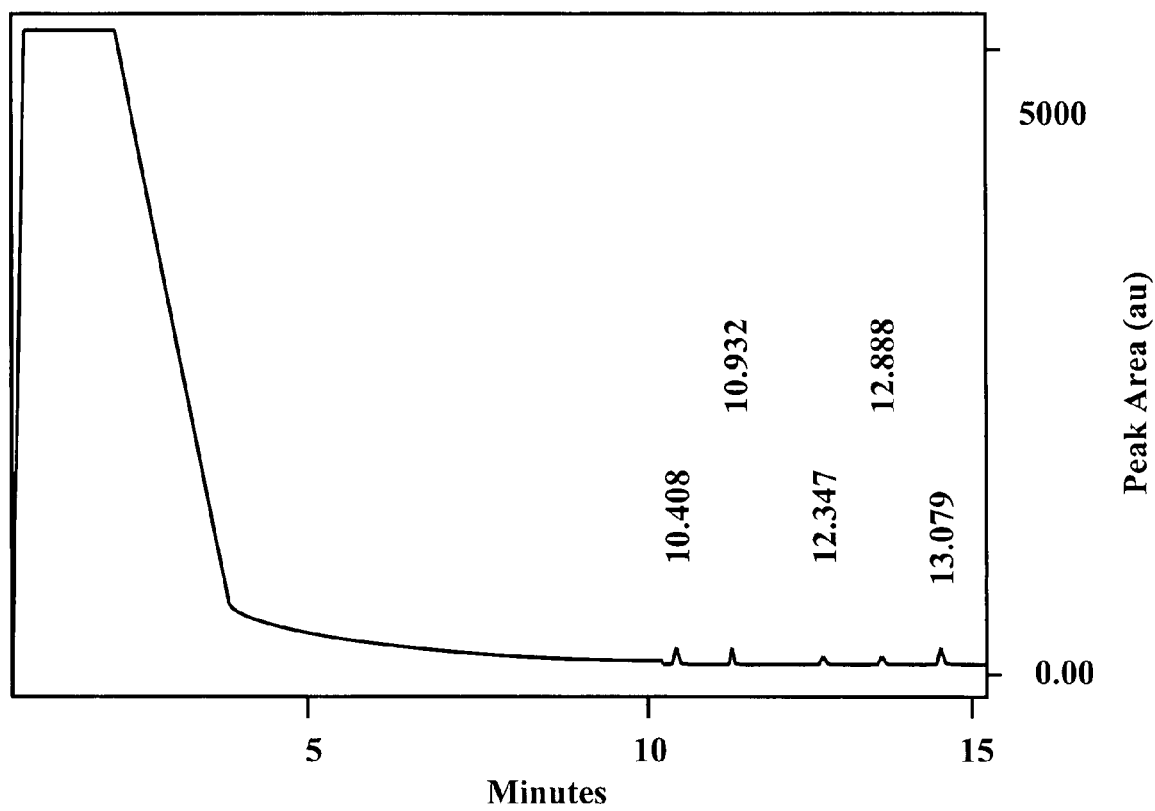
FIG. 3 illustrates the gas chromatographic profile of wax from the insect Ericerus pela before hydrolysis with no polycosanol present.
Figure 4:
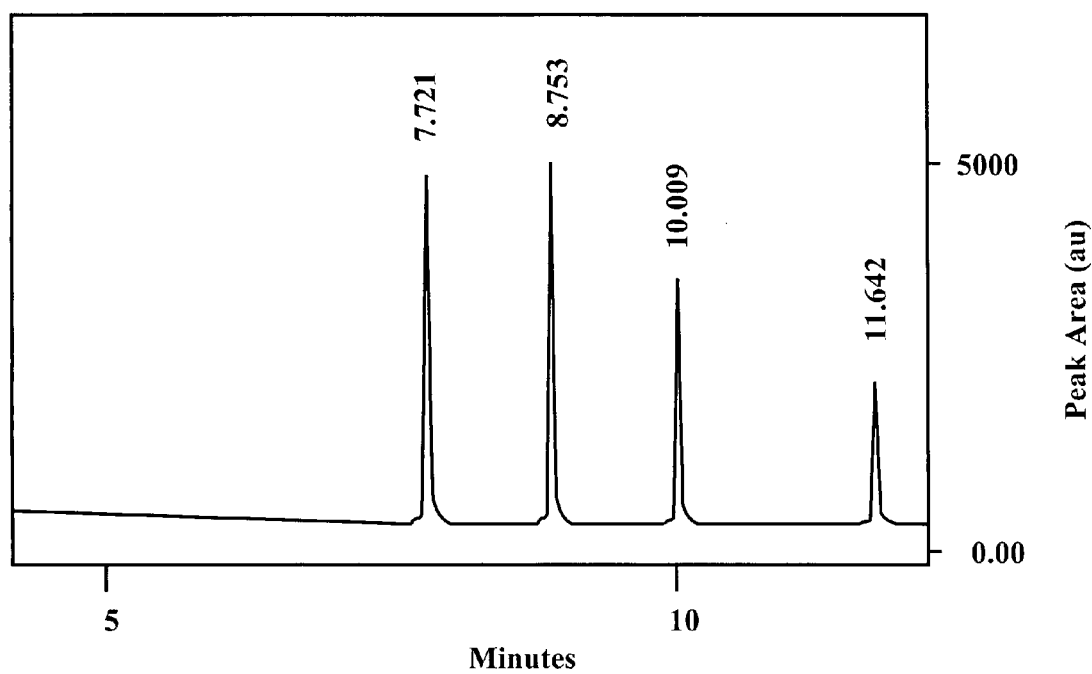
FIG. 4 depicts the gas chromatographic profile of wax from the insect Ericerus pela after hydrolysis. The hydrosylate contains tetracosanol (7.7 min.), hexacosanol (8.7 min.), octacosanol (10 min.) and triacontanol (11.6 min.).
Figure 5:
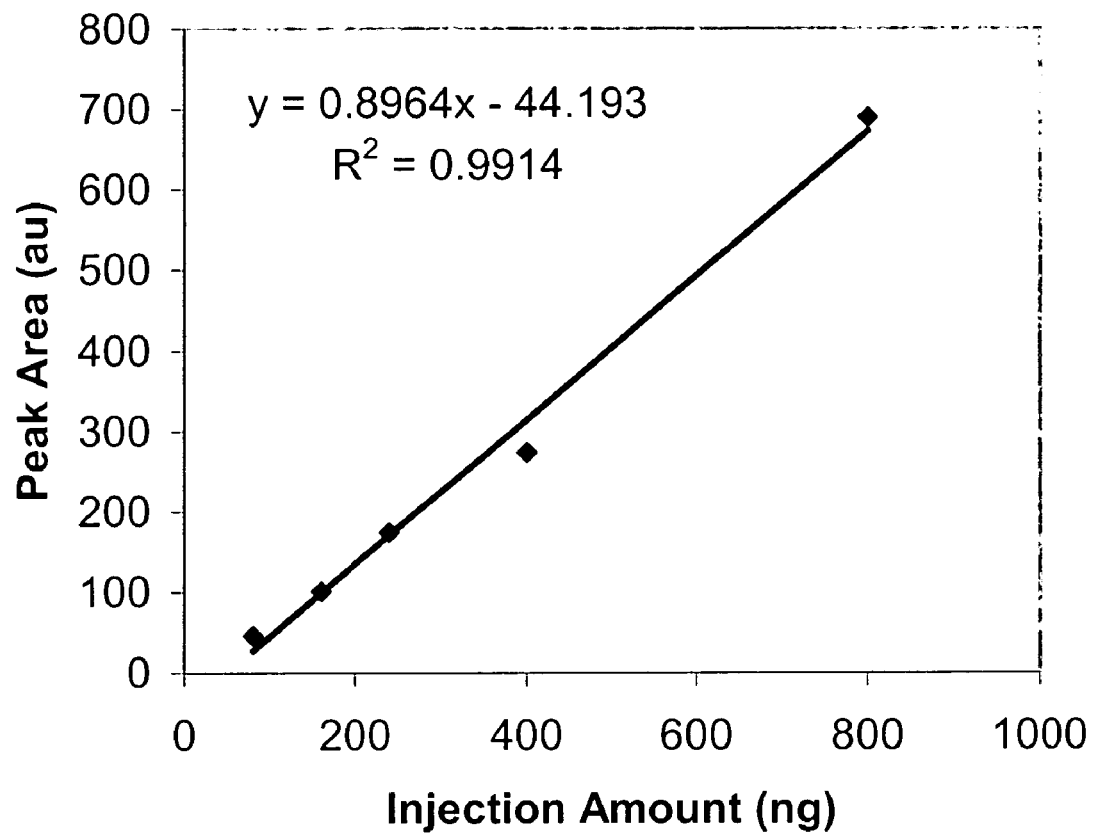
FIG. 5 depicts the linear range of tetracosanol in the GC analysis.
Figure 6:
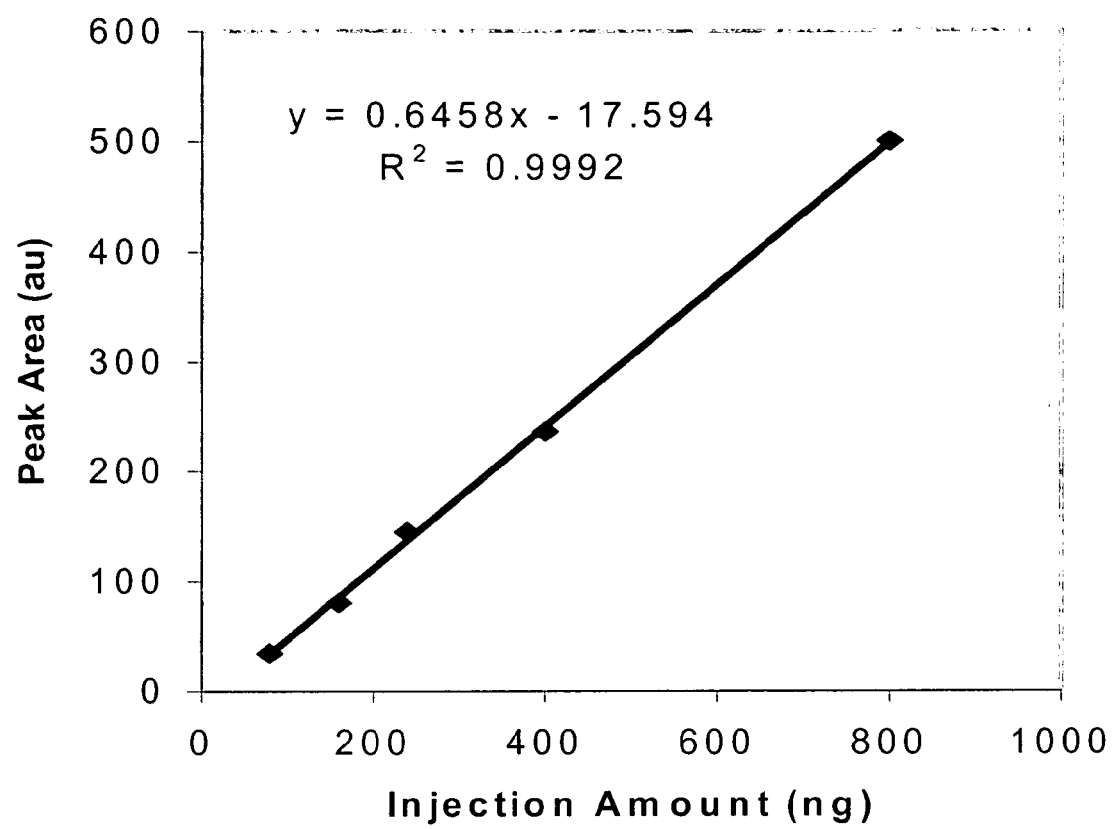
FIG. 6 illustrates the linear range of hexacosanol in the GC analysis.
Figure 7:
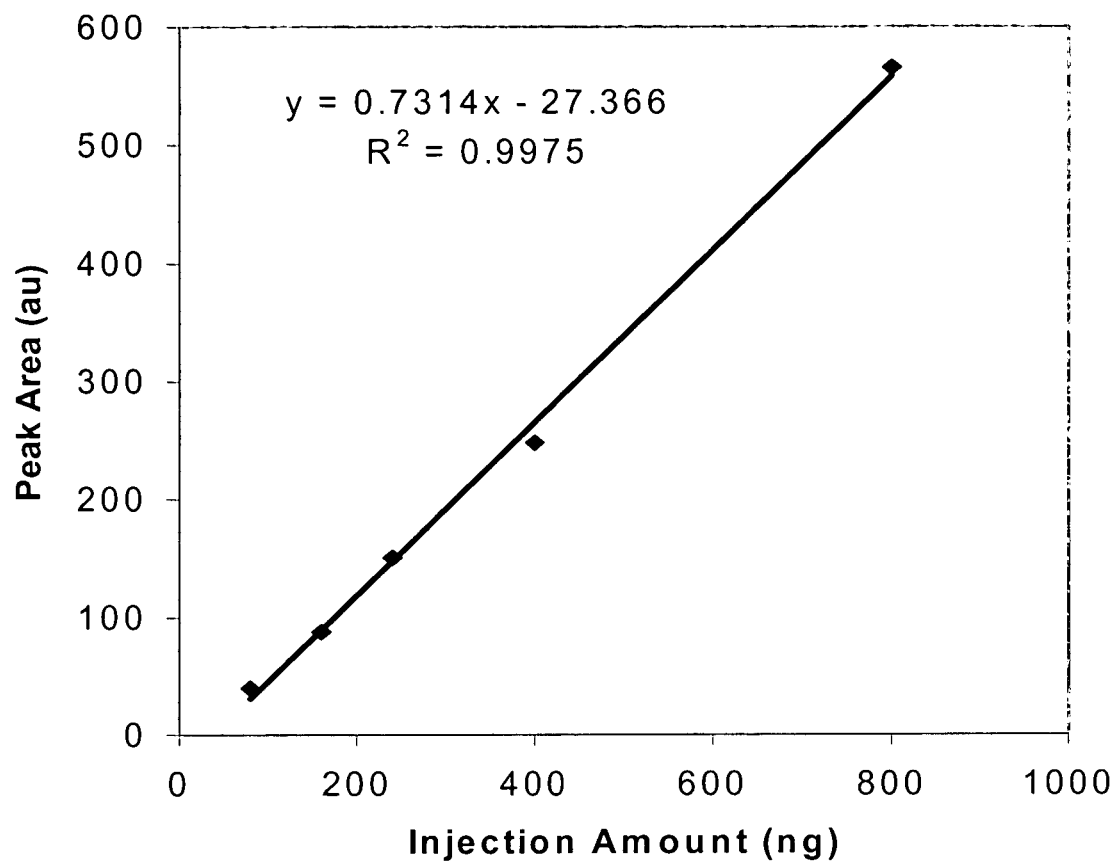
FIG. 7 depicts the linear range of triacontanol in the GC analysis.
Figure 8:
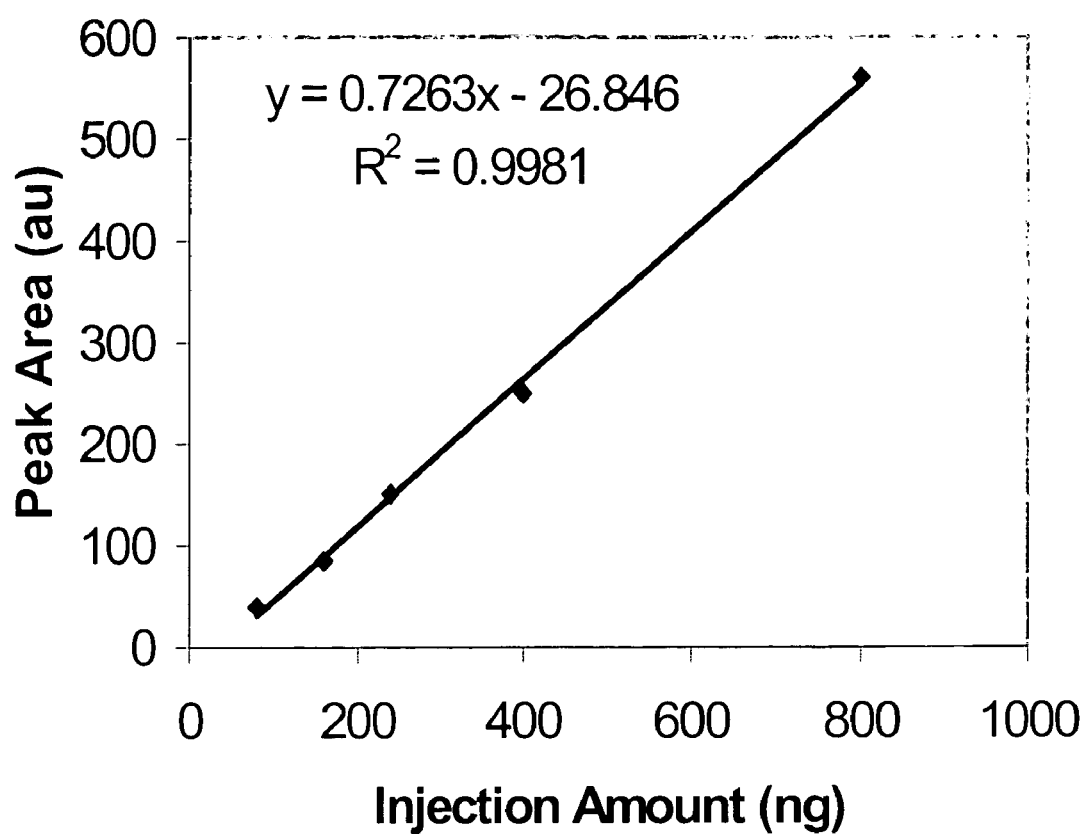
FIG. 8 depicts the linear range of octacosanol in the GC analysis.

The present invention includes a method for the preparation of a unique profile of primary aliphatic alcohols, having 24 to 30 carbon atoms, from the wax secreted by the insect Ericerus pela. Included in the present invention is the composition of matter, referred to herein as "polycosanol" produced by the method of this invention. The polycosanol composition produced by the method of this invention is comprised primarily of only four primary aliphatic alcohols, tetracosanol, hexacosanol, octacosanol and triacontanol. Further included in this invention is the use of said composition of matter for the prevention and treatment of obesity, syndrome X, diabetes, hypercholesterolemia, atherosclerotic complications, ischemia and thrombosis.

Various terms are used herein to refer to aspects of the present invention. To aid in the clarification of the description of the components of this invention, the following definitions are provided.

It is to be noted that the term "a" or "an" entity refers to one or more of that entity. As such, the terms "a" or "an," "one or more" and "at least one" are used interchangeably herein.

As used herein the term "higher primary aliphatic alcohols" refers to primary aliphatic alcohols having 24 to 30 carbon atoms (C24–C30). More specifically, the term higher primary aliphatic alcohols refers to the four alcohols—tetracosanol, hexacosanol, octacosanol and triacontanol.

As used herein the term "polycosanol" refers to the mixture of higher primary aliphatic alcohols derived from the hydrolysis of the wax of the insect Ericerus pela.

"Therapeutic" as used herein, includes treatment and/or prophylaxis. When used, therapeutic refers to humans, as well as, other animals.

"Pharmaceutically or therapeutically effective dose or amount" refers to a dosage level sufficient to induce a desired biological result. That result may be the delivery of a pharmaceutical agent, alleviation of the signs, symptoms or causes of a disease or any other desired alteration of a biological system.

A "host" is a living subject, human or animal, into which the compositions described herein are administered.

Note, that throughout this application various citations are provided. Each citation is specifically incorporated herein in its entirety by reference.

The method of the present invention for preparing a unique profile of primary aliphatic alcohols is comprised of the steps of (a) hydrolyzing the melted wax obtained from the insect *Ericerus pela* with a base solution; (b) neutralizing the basic hydrosylate obtained from step (a) to yield a composition of matter comprised of polycosanols; and (c) optionally extracting the hydrosylate without neutralization with an organic solvent to obtain a higher purity polycosanol composition. In another embodiment of the instant invention, the method of the invention further comprises the step of (d) purifying the hydrolyzed product obtained in step (c) by recrystallization.

The method of the present invention is based on the homogeneous phase hydrolysis/saponification of the wax isolated from the insect *Ericerus pela*. The wax is first melted at a temperature of between 80° C. to 100° C. and then treated with a base in either an aqueous or an alcoholic solution. The ratio of the amount of wax to the volume of solvent is very critical to ensure the completion of the hydrolysis reaction. In stead of less than a 1:1 ratio of wax:solvent, the current invention uses at least a 1:1 and up to a 1:12 ratio of wax:solvent. In the absence of sufficient solvent, the free polycosanols will begin to solidify during the middle of the reaction and will trap a significant amount of the non-hydrolyzed esters in the solid. This will result in a low yield of highly impure final product, due to the high solubility of these non-hydrolyzed esters in organic solvents. Any base used by those of skill in the art can be used to perform the hydrolysis. In a preferred embodiment, the base is selected from an alkaline earth hydroxide including, but not limited to NaOH, KOH or CaOH.

As noted above, the hydrolysis can be performed in an aqueous solution or an alcoholic solution. In a preferred embodiment, the hydrolysis is performed in an alcoholic solution because the wax is more soluble in alcohol than in water. Any primary, secondary or tertiary alcohol having from one to ten carbon atoms can be used as the solvent including, but not limited to methanol, ethanol, propanol and n-butanol.

The concentration of the hydroxide solution must be selected such that the ratio in weight of the corresponding hydroxide to that of the wax to be processed is greater than 5%. In a preferred embodiment, the weight ratio of hydroxide to wax is from about 8% to 40%, most preferably the weight ratio of hydroxide to wax is about 25%. The use of a greater percentage of hydroxide to perform the hydrolysis reaction is novel to the current application. It will not only maintain higher pH value that leads to the completion of the hydrolysis reaction, but also plays a very critical role in obtaining high purity polycosanol products. The saponification reaction is allowed to proceed for a time period of at least 30 minutes to 40 hours. Preferably, the reaction is allowed to proceed for a time period of about 2 to 6 hours. The hydrolysis/saponification process is facilitated by mechanic agitation and heating both with and without pressurization. The reaction temperature range is between 50° C. to 200° C. In a preferred embodiment, the reaction is performed at 100° C. and ambient pressure for approximately six hours.

Upon completion of the hydrolysis the hydrosylate is neutralized and the residual solvent is removed to provide a solid residue comprised of a composition of matter of low purity polycosanols. The hydrosylate can be neutralized using any organic or inorganic acid known to one of skill in the art to perform such a neutralization. In one embodiment, the acid is selected from the group including, but not limited to acetic acid, sulfuric acid, phosphoric acid, choleric acid, nitric acid and hydrochloric acid. In one embodiment of the invention, the hydrosylate reaction mixture is adjusted to a pH of about 1 to 6. After neutralization, the residual solvent is removed using a method including, but not limited to filtration, centrifugation, decanting, evaporation, concentration, crystallization or a combination thereof.

The solid residue comprised of a composition of matter of low purity polycosanols obtained without neutralization can optionally be further purified by extraction with an organic solvent. Contrary to reported methods, which extract the polycosanol compositions subsequent to neutralization of the reaction mixture, the current invention intentionally maintains the strongly basic conditions by significantly increasing the amount of base used in the hydrolysis reaction and extracting without neutralization. The excess base remaining after completion of the hydrolysis, keeps the higher primary aliphatic fatty acids, mainly hexacosanic acid in the form of their sodium salts. Since the water solubility of hexacosanic acid sodium salt is much higher than its solubility in organic solvents, this will prevent hexacosanic acid from extracting into the organic solvent. This results in a polycosanol product that has a much greater purity.

The extraction can be performed using any method of extraction known to those of skill in the art. In one embodiment the extraction is performed by liquid-liquid partition or solid-liquid extraction. The extraction solvent is selected from the group of organic solvents including, but not limited to hydrocarbons having 6 to 9 carbon atoms, such as, pentane, hexane, heptane, octane or a mixture of hydrocarbons such as petroleum ether; ketones having 3 to 8 carbon atoms, such as, acetone, pentanone, 2-methyl pentanone hexanone, methyl ethyl ketone, methyl butyl ketone and/or heptanone; alcohols having 1 to 5 carbon atoms, such as methanol, ethanol, n-propanol, 2-propanol, n-butanol, 2-butanol, n-pentanol and tert-butanol; halogenated solvents, such as dichloromethane, 1,2-dichloroethane, chloroform, carbon tetrachloride, tricholoroethane, 1,2-dichloropropane or 1,2,3-trichloropropane or aromatic solvents, such as benzene, phenyl, toluene and p-methyl toluene as well as mixtures thereof. The polycosanols are selectively extracted with the organic solvent to provide a polycosanol composition of higher purity.

In one embodiment of the present invention, the polycosanol product obtained from the extraction is further purified by means of recrystallization.

Included in the present invention are the polycosanol compositions of matter prepared and isolated by the method of this invention. The long chain aliphatic alcohol portions of the polycosanol compositions prepared and isolated by the methods of this invention are comprised primarily of the four primary aliphatic alcohols 1-hexacosanol (20%–50%), 1-octacosanol (15%–45%), 1-triacontanol (2%–10%) and 1-tetracosanol (approximately 1%–9%). The total amount of long chain aliphatic alcohols in these compositions can be anywhere in the range of 35% to 100%, depending on the level of purification of the crude extract obtained from step (b) of the described method. In one embodiment, the composition of matter is isolated following hydrolysis of the wax and neutralization with no further purification. This composition is comprised of approximately 35–55% of the long chain primary aliphatic alcohols of interest. The major components of this composition are: 1-hexacosanol (~20–30%), 1-octacosanol (~15–25%), with two minor compounds: 1-triacontanol (~2–4%) and 1-tetracosanol (~1–3%). In another embodiment, the composition of matter is isolated following hydrolysis of the wax, without neutralization and further purification via extraction with an organic solvent. In this embodiment the composition of matter is comprised of approximately 75–100% of the long chain primary aliphatic alcohols. The major components of this composition are 1-hexacosanol (~30–50%), 1-octacosanol (~25–45%), with two minor polycosanols: 1-triacontanol (~4–10%) and 1-tetracosanol (~3–9%). As noted above, the alcoholic mixtures obtained from *Ericerus pela* wax in accordance with the present invention can be distinguished from all other currently known sources of polycosanols. Table 1, below highlights the differences between the compositions isolated from sugar cane and bee wax, which are currently the major commercially available sources of polycosanols, with the composition isolated according to the method of this invention. With reference to Table 1, it can be seen that the composition of matter isolated from *E. pela* has a much greater percentage of hexacosanol (C26) (~45%) than either sugar cane (~6–9%) or bee wax (~7–12%). The polycosanol isolated from *E. pela* also has a somewhat lower percentage of triacontanol (C30).

Further included in this invention is the use of the compositions of matter produced for the prevention and treatment of obesity, syndrome X, diabetes, hypercholesterolemia, atherosclerotic complications, ischemia and thrombosis.

Various delivery systems are known in the art and can be used to administer the therapeutic compositions of the invention, e.g., aqueous solution, encapsulation in liposomes, microparticles, and microcapsules.

Therapeutic compositions of the invention may be administered parenterally by injection, although other effective administration forms, such as intraarticular injection, inhalant mists, orally active formulations, transdermal iontophoresis or suppositories are also envisioned. One preferred carrier is physiological saline solution, but it is contemplated that other pharmaceutically acceptable carriers may also be used. In one preferred embodiment, it is envisioned that the carrier and polycosanol composition constitute a physiologically-compatible, slow release formulation. The primary solvent in such a carrier may be either aqueous or non-aqueous in nature. In addition, the carrier may contain other pharmacologically-acceptable excipients for modifying or maintaining the pH, osmolarity, viscosity, clarity, color, sterility, stability, rate of dissolution, or odor of the formulation. Similarly, the carrier may contain still other pharmacologically-acceptable excipients for modifying or maintaining the stability, rate of dissolution, release or absorption of the ligand. Such excipients are those substances usually and customarily employed to formulate dosages for parental administration in either unit dose or multi-dose form.

Once the therapeutic composition has been formulated, it may be stored in sterile vials as a solution, suspension, gel, emulsion, solid, or dehydrated or lyophilized powder; or directly capsulated and/or tableted with other inert carriers for oral administration. Such formulations may be stored either in a ready to use form or requiring reconstitution immediately prior to administration. The manner of administering formulations containing the compositions for systemic delivery may be via enteral, subcutaneous, intramuscular, intravenous, intranasal or vaginal or rectal suppository.

The amount of the composition that will be effective in the treatment of a particular disorder or condition will depend on the nature of the disorder of condition, which can be determined by standard clinical techniques. In addition, in vitro or in vivo assays may optionally be employed to help identify optimal dosage ranges. The precise dose to be employed in the formulation will also depend on the route of administration, and the seriousness or advancement of the disease or condition, and should be decided according to the practitioner and each patient's circumstances. Effective doses may be extrapolated from dose-response curved derived from in vitro or animal model test systems. For example, an effective amount of the composition of the invention is readily determined by administering graded doses of the composition of the invention and observing the desired effect.

The method of treatment according to this invention comprises administering internally or topically to a host in need thereof a therapeutically effective amount of the polycosanol composition isolated according to the method of this invention. The purity of the polycosanol composition administered includes, but is not limited to 0.01% to 100%, depending on the methodology used to obtain the compound(s). In a preferred embodiment doses of the polycosanol and pharmaceutical compositions containing that same are an efficacious, nontoxic quantity generally selected from the range of 0.01 to 200 mg/kg of body weight. Persons skilled in the art using routine clinical testing are able to determine optimum doses for the particular ailment being treated.

This invention includes an improved method for isolating and purifying polycosanol compositions from a novel source, the wax of the insect *E. pela*. 1 describes gas chromatographic (GC) method used to quantify the various polycosanols present in the compositions isolated. Examples 2–6 describe various methods used to hydrolyze/saponify the wax and the profile of the composition obtained using each method. Examples 7–12 describe various methods for further purifying the initial hydrolyzed extract isolated and the profile of the composition obtained using each method. Example 13 describes an experiment performed to determine the effect of the composition of this invention on lipid levels. With reference to Table 13, it can be seen that HDL levels were raised significantly in the mice treated with both 2.7 mg/kg/day (15 mg equivalent human dose, $p<0.05$) and 5.5 mg/kg/day (30 mg equivalent human dose, $p<0.01$) over a six month period. The data also shows that total cholesterol and LDL levels were reduced.

TABLE 1

Composition of polycosanol from different natural sources

|  | Sugar Cane Wax | Bee Wax | Insect Wax |
| --- | --- | --- | --- |
| Existing Form | Primarily esters | Free alcohols and esters | Esters |
| Hydrolysis | Required | Not necessarily required | Required |
| Alcohol | Percentage (w/w %) | Percentage (w/w %) | Percentage (w/w %) |
| 1-tetracosanol | 0.5–1 | 1–4 | 3–5 |
| 1-hexacosanol | 5.5–8.5 | 7–12 | 44–46 |
| 1-heptacosanol | 2–3.5 | 1–4 | 0 |
| 1-octacosanol | 60–70 | 30–60 | 35–40 |

TABLE 1-continued

Composition of polycosanol from different natural sources

|  | Sugar Cane Wax | Bee Wax | Insect Wax |
|---|---|---|---|
| 1-nonacosanol | 0.4–1.2 | 2–5 | 0 |
| 1-triacontanol | 10–15 | 16–26 | 4–8 |
| 1-dotriacontanol | 4–6 | 13–22 | Trace |
| 1-tetratriacontanol | 0.4–2 | 2–6 | 0 |

The following examples are provided for illustrative purposes only and are not intended to limit the scope of the invention.

EXAMPLES

Example 1

Quantification of Polycosanol Using Gas Chromatography

The method for quantifying polycosanol was developed using a Shimazu Gas Chromatograph (GC-17A). The separation was carried out on one of the following GC columns: XTI-5 (bonded 5% phenyl, 30 meters, 0.25 mm ID and 0.5 µm thick) or DB-5HT (fused silica gel, 30 meters, 0.25 mm ID and 0.1 µm film). The carrying gas was helium at a flow rate 3.0 mL/min. The temperature settings were as follows: injector 375° C., detector 375° C., column oven starting at 190° C. (1 minute) and increasing to 315° C. at the rate of 35° C./minute. The column oven temperature was then kept at 315° C. for 10 minutes. Sample and standards were dissolved in THF at a concentration between 50 to 200 ng/µL and directly injected onto the top of column without splitting at a volume of 2 µL per injection. The eluted alcohols were detected with a FID detector. Compound identification was based on retention time derived from individual alcohol standards. A calibration curve was measured for each standard at seven different concentrations (50, 100, 150, 250, 400, 600 and 800 ng). For wax sample quantification, hexacosanol was utilized as an external standard and response factors were calculated based on the concentrations and GC peak area as 0.62/0.94/1.0/1.25/1.98 (C24/C26/C27/C28/C30).

Example 2

Hydrolysis of *Ericerus pela* Insect Wax in Ethanol

*Ericerus pela* insect wax (25 g) was melted at a temperature between 80 to 100° C. Sodium hydroxide solution (5 g dissolved in 5 mL of water) was added to the wax with 95 mL of 30% ethanol. The mixture was stirred and refluxed for 4 hours and then allowed to cool to room temperature. The white solid obtained was filtered and washed twice with water (500 mL), then neutralized with glacial acetic acid (5 mL) and washed with water (3x) until neutral. As much as 22.5 g of crude polycosanol was obtained at a yield of 90%, containing four major fatty alcohols (1-tetracosanol, 1-hexacosanol, 1-octacosanol and 1-triaconsanol) having a purity of 62.2%. The alcohol profile of the product is set forth in Table 2 below.

TABLE 2

Long chain alcohol profile of polycosanol product (hydrolysis in EtOH)

| Component | Percentage (w/w %) |
|---|---|
| 1-tetracosanol | 2.7 |
| 1-hexacosanol | 30.1 |
| 1-octacosanol | 24.5 |
| 1-triacontanol | 4.9 |

Example 3

Hydrolysis of *Ericerus pela* Insect Wax in Methanol

*Ericerus pela* insect wax (100 g) was melted at a temperature between 80 to 100° C. Sodium hydroxide solution (25 g dissolved in 30 mL of water) was added into the wax with 290 mL of 52.5% methanol. The saponification reaction was allowed to proceed for a period of five hours with heating and stirring. The mixture was cooled to room temperature and filtered to obtain a white solid. The solid was washed with water (2x), neutralized with sulfuric acid (50 mL, 20%, w/w) and washed with water (3x). The polycosanol product (91 g) was obtained at a yield 91% having a purity of 59.0% based on four major fatty alcohols (1-tetracosanol, 1-hexacosanol, 1-octacosanol and 1-triaconsanol). The alcohol profile of the product is set forth in Table 3 below.

TABLE 3

Long chain alcohol profile of polycosanol product (hydrolysis in MeOH)

| Component | Percentage (w/w %) |
|---|---|
| 1-tetracosanol | 2.5 |
| 1-hexacosanol | 28.3 |
| 1-octacosanol | 24.1 |
| 1-triacontanol | 4.1 |

Example 4

Hydrolysis of *Ericerus pela* Insect Wax in 1-Propanol

*Ericerus pela* insect wax (500 g) was melted at a temperature between 80 to 100° C. Sodium hydroxide solution (100 g dissolved in 100 mL of water) was added to the wax with 1900 mL of 50% 1-propanol. The saponification reaction was allowed to proceed for a period of six hours with stirring and heating. The mixture was cooled to room temperature and filtered to obtain a white solid. The solid was washed with water (2x), neutralized with hydrochloric acid (300 mL, 25%, w/w) and washed with water until neutral. A total of 460 g of polycosanol was obtained at a yield of 92% having a purity of 55.0% based on four major fatty alcohols (1-tetracosanol, 1-hexacosanol, 1-octacosanol and 1-triaconsanol). The alcohol profile of the product is set forth in Table 4 below.

TABLE 4

Long chain alcohol profile of polycosanol product (hydrolysis in 1-PrOH)

| Component | Percentage (w/w %) |
|---|---|
| 1-tetracosanol | 1.9 |
| 1-hexacosanol | 26.7 |
| 1-octacosanol | 22.9 |
| 1-triacontanol | 3.5 |

Example 5

Hydrolysis of *Ericerus pela* Insect Wax in Water

*Ericerus pela* insect wax (100 g) was melted at a temperature between 80 to 100° C. Sodium hydroxide solution (100 mL, 20%) was added and the reaction mixture was heated with stirring for 4 hours. After 4 hours the reaction mixture was cooled to room temperature and extracted (6×) in a Soxlet extractor using chloroform as the solvent. The combined chloroform solution was evaporated to provide a purified polycosanol (35 g, 35% yield). The product contained four major fatty alcohols (1-tetracosanol, 1-hexacosanol, 1-octacosanol and 1-triaconsanol) at a total concentration of 93.2%. The alcohol profile of the product is set forth below in Table 5.

TABLE 5

Long chain alcohol profile of polycosanol product (hydrolysis in H$_2$O)

| Component | Percentage (w/w %) |
|---|---|
| 1-tetracosanol | 4.1 |
| 1-hexacosanol | 45.6 |
| 1-octacosanol | 36.2 |
| 1-triacontanol | 7.3 |

Example 6

Hydrolysis of *Ericerus pela* Insect Wax in n-Butanol

*Ericerus pela* insect wax (25 g) was melted at a temperature between 80 to 100° C. Sodium hydroxide solution (7.5 g of sodium hydroxide dissolved in 5 mL of water) was added with 95 mL of 52.5% n-butanol. The saponification reaction was allowed to proceed for a period of 4.5 hours with stirring and heating. The mixture was cooled to room temperature and filtered to obtain a white solid. The solid was washed with water (2×), neutralized with concentrated phosphoric acid (5 mL) and washed with water (3×) until neutral. A total of 22 g of polycosanol (88% yield) was obtained having a purity of 60.7% based on four major fatty alcohols (1-tetracosanol, 1-hexacosanol, 1-octacosanol and 1-triaconsanol) as shown in Table 6.

TABLE 6

Long chain alcohol profile of polycosanol product (hydrolysis in n-BuOH)

| Component | Percentage (w/w %) |
|---|---|
| 1-tetracosanol | 2.2 |
| 1-hexacosanol | 29.4 |
| 1-octacosanol | 25.1 |
| 1-triacontanol | 4.0 |

Example 7

Isolation of Polycosanol from *Ericerus pela* Insect Wax by Extraction with Ethyl Acetate

*Ericerus pela* insect wax (25 g) was melted at 80–100° C. Potassium hydroxide (5 g) dissolved in 300 mL of 25% ethanol in water was added to the melted wax. The reaction mixture was maintained at 80–100° C. for 4.5 hours with stirring and heating. The basic reaction solution was then cooled to room temperature and extracted with ethyl acetate (10×). The ethyl acetate extracts were combined and evaporated to provide purified polycosanol (6 g, 24% yield), containing four major fatty alcohols (1-tetracosanol, 1-hexacosanol, 1-octacosanol and 1-triaconsanol) having a purity of 95.0%. The alcohol profile of the product is set forth in Table 7 below.

TABLE 7

Long chain alcohol profile of polycosanol product (EtOAc extraction)

| Component | Percentage (w/w %) |
|---|---|
| 1-tetracosanol | 4.2 |
| 1-hexacosanol | 43.7 |
| 1-octacosanol | 39.9 |
| 1-triacontanol | 7.2 |

Example 8

Isolation of Polycosanol from *Ericerus pela* Insect Wax by Extraction with Hexane

*Ericerus pela* insect wax (500 g) was melted at 100–105° C. Sodium hydroxide (150 g) dissolved in 1500 mL of water was added to the melted wax and the solution was heated with stirring for 5 hours. After five hours a white solid was obtained by filtration. The solid was extracted for 12 hours in a Soxlet extractor using hexane as the solvent. The hexane solution was cooled to room temperature, resulting in the crystallization of the polycosanol product. The crystallized product was then filtered and recrystallized in methanol. Upon recrystallization polycosanol (165 g, 33% yield) was obtained, having a purity 92.3% aliphatic alcohols. The melting point of the mixture was 85–91° C. The fatty acid profile of this product is set forth in Table 8 below.

TABLE 8

Long chain alcohol profile of polycosanol product (hexane extraction)

| Component | Percentage (w/w %) |
|---|---|
| 1-tetracosanol | 4.0 |
| 1-hexacosanol | 45.8 |
| 1-octacosanol | 38.3 |
| 1-triacontanol | 4.0 |

Example 9

Isolation of Polycosanol from *Ericerus pela* Insect Wax by Extraction with Chloroform

*Ericerus pela* insect wax (200 g) was melted at 80–100° C. Sodium hydroxide (60 g) dissolved in 500 mL of water was added to the melted wax and the reaction was allowed to proceed for a period of 4 hours with stirring and heating. The solid obtained after the reaction was completed, was filtered and extracted for 10 hours in a solid-liquid extraction system using chloroform as the solvent. The solution was cooled to room temperature, resulting in the crystallization of the polycosanol. The crystallized product was then filtered and recrystallized in methanol/chloroform (3/1) mixture. Polycosanol (75 g, 37.5% yield) was obtained having a purity of 93.2%. The melting point of the mixture ranged from 86 to 90° C. Table 9 sets forth the composition of the polycosanol product.

TABLE 9

Long chain alcohol profile of polycosanol product ($CHCl_3$ extraction)

| Component | Percentage (w/w %) |
| --- | --- |
| 1-tetracosanol | 4.1 |
| 1-hexacosanol | 42.4 |
| 1-octacosanol | 39.7 |
| 1-triacontanol | 7.0 |

Example 10

Isolation of Polycosanol from *Ericerus pela* Insect Wax by Extraction with Tetrahydrofuran (THF)

*Ericerus pela* insect wax (1000 g) was melted at 90–110° C. and potassium hydroxide (300 g) dissolved in 1500 mL of water was added. The saponification reaction was allowed to proceed for 120 minutes with stirring and heating. A white solid was obtained, which was filtered from the reaction mixture and then extracted with THF in a solid-liquid extracting system. The THF extract was evaporated and the residual solid was crystallized in petroleum ether to yield 355 g of polycosanol (35.5% yield) having a purity of 89.4%. The melting point of the mixture was 81 to 85° C. Table 10 sets forth the alcohol composition of the product.

TABLE 10

Long chain alcohol profile of polycosanol product (THF extraction)

| Component | Percentage (w/w %) |
| --- | --- |
| 1-tetracosanol | 4.2 |
| 1-hexacosanol | 43.5 |
| 1-octacosanol | 37.2 |
| 1-triacontanol | 4.4 |

Example 11

Isolation of Polycosanol from *Ericerus pela* Insect Wax by Extraction with Methylene Chloride

*Ericerus pela* insect wax (500 g) was melted at 90–100° C. and sodium hydroxide (120 g) dissolved in 1000 mL of water was added. The reaction mixture was stirred and heated for a period of 6 hours. The white solid produced was filtered and extracted with methylene chloride for a period of 12 hours in a conventional solid-liquid extraction system. The extraction solution was cooled to room temperature and the solid obtained was recrystallized in ethanol to yield 143 g of polycosanol (28.6% yield). The crystallized product contained total 91.8% fatty alcohols, having a melting point between 83–86° C. Table 11 shows the profile of the polycosanol product.

TABLE 11

Long chain alcohol profile of polycosanol product ($CH_2Cl_2$ extraction)

| Component | Percentage (w/w %) |
| --- | --- |
| 1-tetracosanol | 4.8 |
| 1-hexacosanol | 41.4 |
| 1-octacosanol | 40.2 |
| 1-triacontanol | 5.4 |

Example 12

Isolation of Polycosanol from *Ericerus pela* Insect Wax by Extraction with Petroleum Ether

*Ericerus pela* insect wax (500 g) was melted at 100–110° C. and sodium hydroxide (150 g) dissolved in 700 mL of water was added. The mixture was stirred and heated for 3 hours and then filtered. The solid obtained was extracted with petroleum ether for 16 hours in a solid-liquid extractor and the extraction solution was then cooled to room temperature and filtered. The solid was crystallized to yield polycosanol (150 g, 30% yield) having a purity of 95.0%. The melting point of the mixture ranged from 83–87° C. Table 12 shows the long chain aliphatic alcohol profile of the crystallized product.

TABLE 12

Long chain alcohol profile of polycosanol product (pet. ether extraction)

| Component | Percentage (w/w %) |
| --- | --- |
| 1-tetracosanol | 4.7 |
| 1-hexacosanol | 43.4 |
| 1-octacosanol | 41.5 |
| 1-triacontanol | 5.4 |

Example 13

Effect of Polycosanol Composition on Lipid Levels

Animal Model: C57BL/J-6 (Daihan BioLink, Korea) mice fed a high fat, cholesterol and cholic acid diet (TD-88051, supplemented with 15.8% fat, 1.25% cholesterol, and 0.5% Na-cholate, Harlan Teklad, USA). The lipid profile (mg/dl) in the high-fat diet induced hyperlipidemic C57BL/6J mice (n=5/group) following treatment for 6 months is set forth in Table 13.

TABLE 13

Lipid Profile Following Treatment with Polycosanol Composition

| Groups* | Cholesterol | Triglycerides | HDL-cholesterol | LDL-cholesterol |
|---|---|---|---|---|
| Control | 366.20 ± 71.06 | 73.80 ± 19.52 | 56.00 ± 8.34 | 84.80 ± 20.04 |
| Poli-90(2.7) | 336.00 ± 52.23 | 71.60 ± 17.56 | 69.00 ± 11.42** | 82.00 ± 12.14 |
| Poli-90(5.5) | 340.00 ± 34.92 | 71.80 ± 20.39 | 80.60 ± 6.58*** | 67.20 ± 10.18 |

*Poli-90(2.7), Polycosanol 90%, 2.7 mg/kg/day, orally for 6 months.
*Poli-90(5.5), Polycosanol 90%, 5.5 mg/kg/day, orally for 6 months.
p value (Student's t-test)
**$p < 0.05$ compared to control group
***$p < 0.01$ compared to control group

The invention claimed is:

1. A polycosanol composition of matter comprised of long chain aliphatic alcohols, wherein said long chain alcohols comprise 1-hexacosanol (20%–50%), 1-octacosanol (15%–45%), 1-triacontanol (2%–10%) and 1-tetracosanol (1%–9%).

2. The composition of claim 1, wherein said composition is derived from the wax of the insect *Ericerus pela*.

3. The composition of claim 1 wherein said long chain aliphatic alcohols comprise 35%–100% of said composition.

4. The composition of claim 1 wherein said long chain aliphatic alcohols comprise 35%–55% of said composition.

5. The composition of claim 1 wherein said long chain aliphatic alcohols comprise 75%–100% of said composition.

* * * * *